US008682452B2

(12) United States Patent  
Minogue et al.

(10) Patent No.: US 8,682,452 B2
(45) Date of Patent: Mar. 25, 2014

(54) FACIAL STIMULATION APPARATUS

(75) Inventors: Conor Minogue, Co. Galway (IE); Shane Ledwidth, Galway (IE)

(73) Assignee: Bio-Medical Research Limited, Galway (IE)

( * ) Notice: Subject to any disclaimer, the term of this patent is extended or adjusted under 35 U.S.C. 154(b) by 95 days.

(21) Appl. No.: 12/592,189

(22) Filed: Nov. 20, 2009

(65) Prior Publication Data

US 2010/0152810 A1 Jun. 17, 2010

Related U.S. Application Data

(63) Continuation of application No. PCT/IB2008/055229, filed on Dec. 11, 2008.

(51) Int. Cl.
*A61N 1/04* (2006.01)
(52) U.S. Cl.
USPC .................................................. 607/139
(58) Field of Classification Search
USPC .......................................... 607/136, 139, 140
See application file for complete search history.

(56) References Cited

U.S. PATENT DOCUMENTS

| | | | |
|---|---|---|---|
| 3,593,422 A | 7/1971 | Jankelson | |
| 3,620,219 A | 11/1971 | Barker | |
| 3,659,614 A | 5/1972 | Jankelson | |
| 3,746,004 A | 7/1973 | Jankelson | |
| 4,817,628 A | 4/1989 | Zealear et al. | |
| 4,865,048 A * | 9/1989 | Eckerson | 607/45 |
| 5,207,231 A * | 5/1993 | Fakhri | 607/134 |
| 7,089,062 B1 * | 8/2006 | Yamada | 607/68 |
| D615,209 S | 5/2010 | Minogue et al. | |
| 2001/0031916 A1 | 10/2001 | Bennett et al. | |
| 2005/0165460 A1 * | 7/2005 | Erfan | 607/57 |
| 2007/0276451 A1 | 11/2007 | Rigaux | |
| 2008/0051852 A1 | 2/2008 | Dietrich et al. | |

FOREIGN PATENT DOCUMENTS

| | | | |
|---|---|---|---|
| CN | 1364071 A | 8/2002 | |
| JP | D136999 | 9/2009 | |
| WO | WO 00/71075 A1 * | 11/2000 | A61N 1/32 |
| WO | WO 03/020363 A1 | 3/2003 | |

OTHER PUBLICATIONS

Supplementary European Search Report for European application No. 09176675.8 (Feb. 1, 2010).

(Continued)

*Primary Examiner* — Eric D. Bertram
*Assistant Examiner* — Elizabeth K So
(74) *Attorney, Agent, or Firm* — Jenkins, Wilson, Taylor & Hunt, P.A.

(57) ABSTRACT

The invention relates to facial stimulation apparatus configured to be worn in a generally horizontal orientation on a user's head, and which uses the ear (14) as an anatomical reference to ensure correct and repeatable placement of skin electrodes (16a,16b) overlying the human facial nerves (1-5) to facilitate Electrical Muscle Stimulation (EMS). The apparatus is provided with a headband (22) having a bend or inclination (24) proximate a distal portion (20) thereof on which the electrodes (16a,16b) are attached. The apparatus is provided with an unambiguous location feature such that a vector component between said location feature and the electrode pair (16a, 16b) is fixed and non-adjustable thus ensuring repeatable and accurate positioning of each electrode (16a, 16b). The apparatus overcomes problems inherent in known devices and, in particular, requires no anatomical knowledge on the part of the end user for its safe and most effective placement.

7 Claims, 10 Drawing Sheets

(56) References Cited

OTHER PUBLICATIONS

Notice of Allowance and Fee(s) Due in Design U.S. Appl. No. 29/315,173 (Dec. 28, 2009).
Procedures for Obtaining a Design Right, JPO website, http://www.jpo.go.jp/cgi/linke.cgi?url=/tetuzuki_e/t_gaiyo_e/de_right.htm, (Printed from worldwideweb on Nov. 18, 2009).
Commonly-assigned, co-pending International Application No. PCT/IB2008/055229 for "Facial Stimulation Appratus", (Unpublished, filed on Dec. 11, 2008).
Beemer, G H et al. "Monitoring neuromuscular transmission" Current Anaesthesia and Critical Care, Churchill Livingstone, London, GB, vol. 7, No. 2, (Apr. 1, 1996) pp. 101-106.
International Search Report for International Application No. PCT/IB2008/055229 (Jul. 6, 2009).
European Search Report for European Patent Application No. EP 09151329.1-2305 (Jun. 29, 2009).
Examination Report for South Korean Patent Application No. 10-2009-0099843 (Jul. 26, 2011).
Office Action for Chinese Application No. 200880132792.0 (May 30, 2013).

* cited by examiner

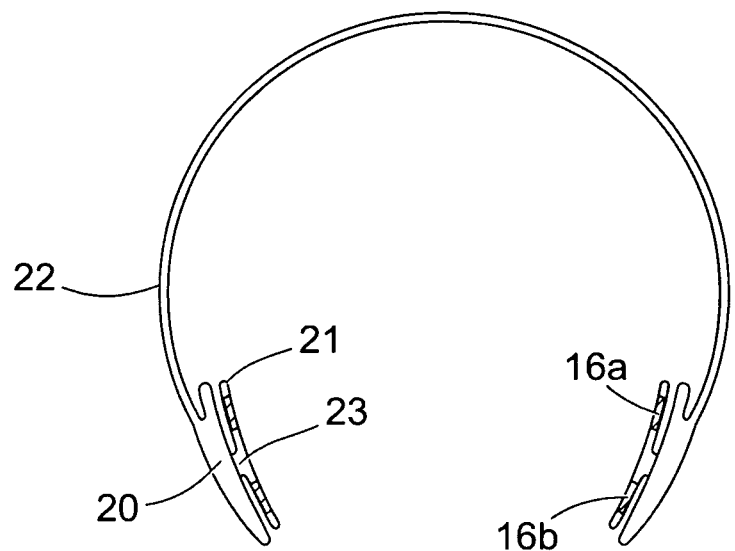
*Fig. 9a*
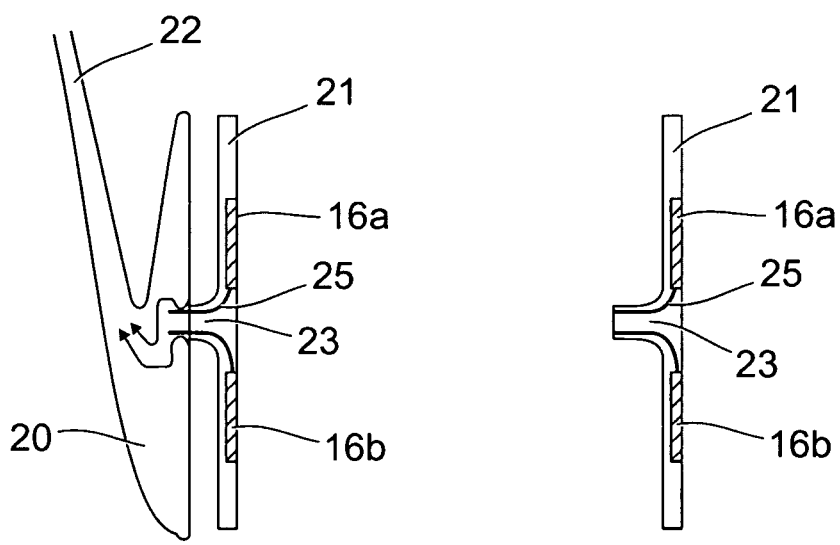
*Fig. 9b*  *Fig. 9c*

FACIAL STIMULATION APPARATUS

RELATED APPLICATIONS

This application is a continuation of PCT International Application No. PCT/IB2008/055229 filed Dec. 11, 2008, the disclosure of which is incorporated herein by reference in its entirety.

The present invention relates to facial stimulation apparatus and a related cosmetic method and particularly, but not exclusively, to wearable apparatus which uses the ear as an anatomical reference to ensure correct and repeatable placement of skin electrodes over the human facial nerves to facilitate cosmetic Electrical Muscle Stimulation (EMS).

The facial muscles determine facial expression and facial shape and therefore exercise of the facial muscles is important in maintaining appearance. It is well known to employ EMS technology on different parts of the human body, for example the abdomen, to prevent muscle disuse atrophy, improve local blood circulation and to improve muscle strength and tone.

However, applying this technology to the face has been difficult for a number of reasons. Firstly, there is a complex network of interconnected muscles on the face and it is difficult to locate skin electrodes with sufficient accuracy to isolate a particular muscle. Furthermore, the ideal electrode location for stimulation of a given facial muscle will differ from person to person due to anatomical variability. There are several systems on the market today which require the user to stick electrodes to the face at various locations to achieve facial stimulation. However, inaccurate placement of skin electrodes can lead to unwanted stimulation of other tissues such as the dental nerves or the nerves controlling movement of the eye. A further problem is that it is difficult to maintain skin electrodes in reliable contact with the face. Facial skin produces natural oils which interfere with the function of adhesive hydrogel materials used on skin electrodes.

Attempts have been made to solve one or more of the aforementioned problems. For example, WO 00/71075 (Maher & Johnson) discloses apparatus in the form of a headset, similar to an audio headset, which is fitted with a pair of adjustable booms each supporting an articulated paddle which in turn supports an electrode pair arranged to contact the face. The boom is adjustable in both its length and angle relative to its anchor point on the headset adjacent an earpiece such that the electrodes are individually positionable over a wide area of the face. Further positional adjustment is possible by virtue of the pivotal attachment of each paddle to the end of the boom through a ball and socket joint.

The disclosure of WO 00/71075 (Maher & Johnson) emphasises the positional adjustability of the electrodes and this aspect was clearly considered to be advantageous. However, this rather elaborate apparatus still suffers from a number of problems.

Firstly, the average end-user of facial stimulation apparatus generally lacks any expertise in the underlying anatomy of the facial muscles and nerves. This lack of anatomical knowledge on the part of the end-user increases the likelihood of incorrect placement of skin electrodes on the face. Whilst written instructions or illustrations for electrode placement may be provided to an end-user, in reality it is very difficult to translate two-dimensional illustrations to the actual three-dimensional reality particularly when inevitable interpersonal anatomical variations are taken into account. As discussed above, the consequences for the end-user of incorrect positioning of skin electrodes on the face can be significant discomfort due to stimulation of inappropriate tissues.

Secondly, by providing a wide degree of adjustability in terms of electrode placement, this will inevitably contribute to a degree of confusion for the end-user when attempting to achieve correct electrode placement. Moreover, it is very difficult for the end-user to know how to combine the numerous adjustable features in a way which achieves a stable positioning of the electrodes such that they are continuously maintained in contact with the skin. Indeed, known mechanisms cannot readily accommodate natural movement of the face since the adjustments are mostly fixed. Electrode separation from the face is a frequent event, interrupting the treatment and causing discomfort and inconvenience.

There is therefore a need for an apparatus which locates appropriately arranged electrodes on the face in a reproducible way, and which requires no anatomical knowledge on the part of the end-user. Having found the correct electrode position, there is a further need that the electrode be maintained in contact with the skin with an appropriate pressure to ensure consistent and comfortable stimulation.

According to a first aspect of the present invention there is provided facial stimulation apparatus for applying an electrical current to the human facial nerves, the apparatus comprising:
(i) a headband;
(ii) a pair of stimulating electrodes attached to a distal portion of the headband;
(iii) a stimulation device connectable to the electrode pair for providing a stimulating current thereto; and
(iv) a location feature for anatomical referencing of the apparatus with respect to an anatomical feature of the ear;
wherein, the apparatus is configured such that, in use, each electrode is presented against the skin overlying the facial nerve anteriorly of the ear; and wherein a vector component between any given point on said location feature and any given point on the electrode pair is fixed and non-adjustable, thus ensuring inevitable positioning of each electrode over the facial nerve anteriorly of the ear, with respect to its anatomical feature.

Optionally, the location feature is defined by one or more tangible features of the apparatus being shaped or otherwise adapted to cooperate with one or more features of the ear.

Optionally, the location feature is defined by a deviation which connects the headband to the distal portion for anatomical referencing with an upper or lower peripheral feature of the ear.

Optionally, the deviation extends out of the general plane within which the remainder of the headband lies.

Additionally or alternatively, the location feature is defined by a mid-line of the distal portion of the headband for anatomical referencing with the earlobe.

Additionally or alternatively, the location feature is defined by a proximal edge of the distal portion of the headband for anatomical referencing with the tragus.

Optionally, the respective electrodes have different shapes and/or surface areas.

According to a second aspect of the present invention there is provided a cosmetic method of applying an electrical current to the human facial nerve comprising the steps of:
(i) providing apparatus comprising a headband;
(ii) providing a pair of stimulating electrodes attached to said distal portion;
(iii) providing a stimulation device connectable to the electrode pair for providing a stimulating current thereto;
(iv) providing a location feature on the apparatus wherein a vector component between any given point on the location feature and any given point on the electrode pair is fixed and non-adjustable;

(v) positioning the headband on the human head; and (vi) referencing the location feature on the apparatus with a peripheral feature on the ear thus causing each electrode on said distal portion to inevitably engage against the skin over the facial nerve anteriorly of the ear, with respect to said peripheral feature.

Optionally, the step of positioning the headband on the human head involves locating the headband around the back of the head such that it lies in a generally horizontal orientation whilst presenting the electrode pair over the facial nerve anteriorly of the ear.

Optionally, the location feature is defined by a deviation of the headband and the method comprises the step of positioning the deviation such that it lies below, and is anatomically referenced to, the earlobe.

Alternatively or additionally, the location feature is defined by a mid-line of the distal portion of the headband and the method comprises the step of positioning the mid-line such that it is aligned with, and is anatomically referenced to, the earlobe.

Alternatively or additionally, the location feature is defined by a proximal edge of the distal portion of the headband and the method comprises the step of positioning the proximal edge such that it lies adjacent, and is anatomically referenced to, the tragus.

Embodiments of the present invention will now be described, by way of example only, with reference to the accompanying drawings, in which.

FIGS. 9a-c show front and cross-sectional views of one example of the apparatus of the present invention indicating the possible positioning of the electrodes within the headband.

Figure 1:
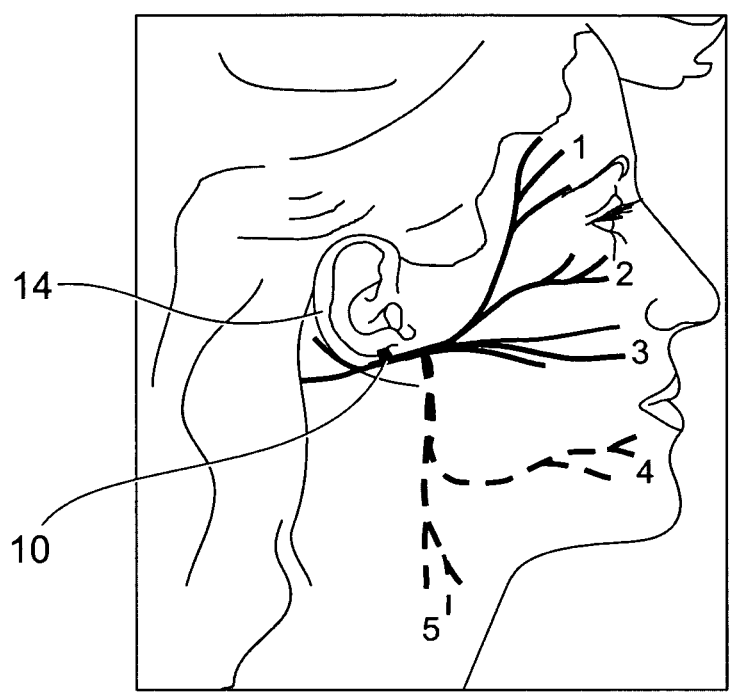
FIG. 1 shows a schematic side view of the human head and illustrates the position of the underlying facial nerve and its constituent branches.

FIG. 1 illustrates the anatomy of the human facial nerves and, in particular, shows the nerve trunk (10) branching into five main components (1-5) just anterior to the ear (14).

Transcutaneous stimulation involves the application of electrodes to the skin overlying the target nerve. The current density and the degree of penetration into the underlying tissue are dependent on both electrode surface area and the separation of an electrode pair. Electrodes which are close together produce minimal penetration into the skin and the underlying tissue since the electric field lines are relatively superficial. Conversely, electrodes which are spaced further apart create deeper field lines and therefore more penetrating currents. This is especially true when the electrodes are spaced over a curved surface. For the stimulation of facial nerves the creation of deep penetrating currents is undesirable since they can affect unintended nerves such as the dental nerves.

The present invention lies partly in the inventor's realisation that, to fulfil the objective of eliciting activity in the motor nerve of the facial muscle, the optimum location to influence the facial nerve is in the region where its constituent branches (1-5) meet the nerve trunk (10) just anterior to the ear (14). At this location, the facial nerve is relatively superficial and therefore allows effective recruitment of the facial nerve without the need for creating deep penetrating currents along its branches (1-5).

Figure 2A:
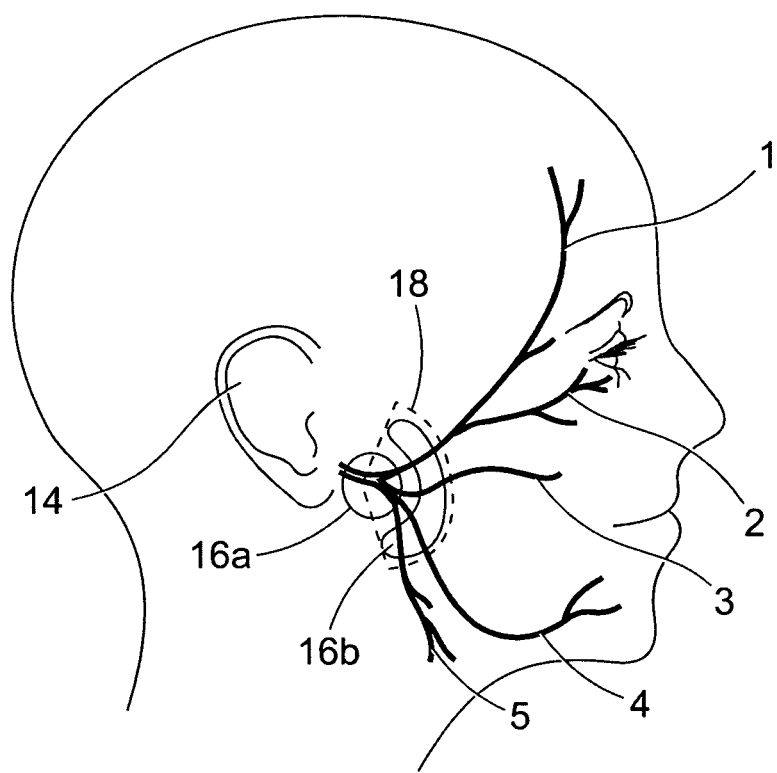
FIG. 2a shows a view similar to that of FIG. 1 indicating the possible positioning of two transcutaneous stimulation electrodes proximate the insertion or trunk of the facial nerves.
Figure 2B:
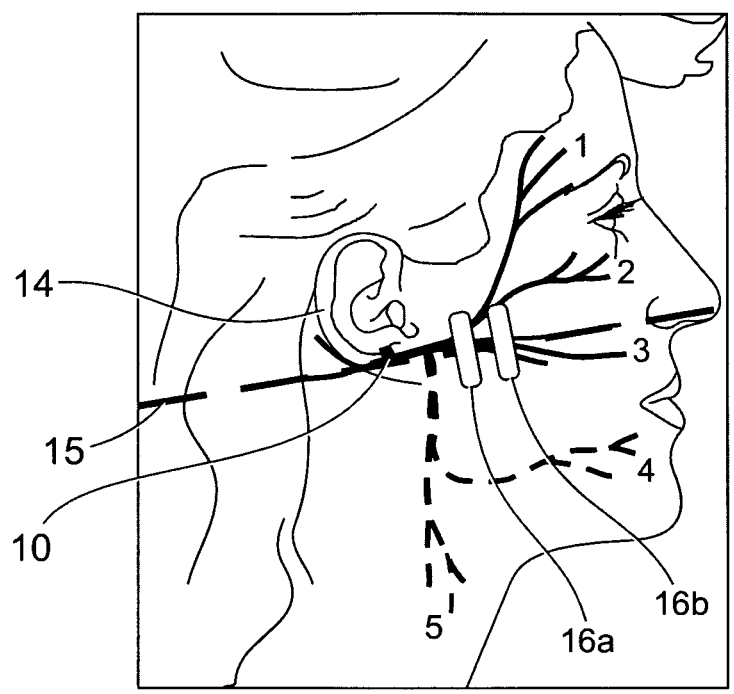
FIG. 2b shows a view similar to that of FIG. 1 indicating possible positioning of two alternative transcutaneous stimulation electrodes proximate the insertion or trunk of the facial nerves.

In two embodiments of the present invention, the arrangement of a pair of electrodes (16a, 16b) forming part of the facial stimulation apparatus is as shown in FIGS. 2a and 2b respectively. Each electrode is covered with a conductive and adhesive hydrogel (not shown) which acts as an electrolyte and also prevents the electrode sliding on the skin. The respective electrodes (16a, 16b) are located against the skin surface at a predetermined localised region of the face which corresponds with the insertion of the branches (1-5) of the facial nerve, just anterior to the ear (14). The shape, size and separation of the electrodes (16a, 16b) are each selected to optimise stimulation of the facial nerve at this localised region.

It has been found to be advantageous to position one electrode (16a) proximate the centre of a notional minor sector of a circle (indicated by dashed lines (18) in FIG. 2a) centred on the insertion of the branches (1-5) of the facial nerve whilst the other electrode (16b) is located proximate the arc of the same minor sector. The first electrode (16a) is substantially circular in shape and the second electrode (16b) is substantially arcuate and follows the line of the aforementioned arc. Furthermore, the first electrode (16a) is smaller in surface area relative to the second electrode (16b). In a preferred arrangement, the first electrode (16a) has a surface area of approximately 4.8 cm$^2$ whilst the second electrode (16b) has an area of approximately 5.6 cm$^2$. The separation the two electrodes (16a, 16b) should generally be at least 4 mm to ensure penetration of the electric field lines into the skin. However, the separation should generally be no more than 12 mm to prevent over-penetration of field lines into the skin.

This particular arrangement of electrodes in terms of their relative positioning, shape, size and separation causes the electrical field lines to diverge from the centre of the notional minor sector of the circle to its peripheral arc (i.e. from the first electrode (16a) to the second electrode (16b)). Accordingly, the arrangement illustrated in FIG. 2a has been found to be particularly suitable for stimulation of a facial nerve tree albeit that the electrodes themselves overlie a relatively small localised region where the constituent branches (1-5) of the facial nerve diverge from the nerve trunk (10).

In the alternative arrangement of FIG. 2b, the electrodes (16a, 16b) are generally rectangular in shape with rounded corners and are in a substantially parallel spaced arrangement. In a preferred arrangement, each electrode (16a, 16b) has a surface area of approximately 5 cm$^2$ and is separated by a distance of approximately 5 mm. In the particular arrangement shown in FIG. 2b, the electrodes (16a, 16b) overly only three of the five nerve branches (1, 2, 3).

Instead of being circular, the first electrode (16a), which is the one closest to the ear in use in FIG. 2a, can be any other suitable shape such as oval or lozenge shaped. The second electrode (16b), which is the one more distal to the ear, may partially envelope the first electrode (16a) whilst being spaced from it. The second electrode (16b) is therefore preferably arcuate in shape. Alternatively, the second electrode (16b) may run substantially parallel to, and at a substantially constant distance from, the outer perimeter of the first electrode (16a).

The facial nerve continues anteriorly after it emerges through the stylomastoid foramen in the skull and extends anterior to the earlobe and tragus through the parotid gland where it divides into its three of its five main branches. The ideal arrangement of the two electrodes is therefore when the angle subtended by the upper and lower limits of the second electrode (16b), relative to the centre of the first electrode (16a), overlaps three or more branches of the facial nerve. Such an electrode arrangement ensures that electric field lines exist beneath the skin to interact with and stimulate at least three branches of the facial nerve. The optimum angle is 180 degrees since this ensures that many pathways of the nerve are covered. However, an angle of 120 degrees also works well and may be more practical for construction.

It is important to realise that while diverging electric field lines are ideal, effective stimulation of the facial nerves can also occur with non-diverging field line patterns. The first and second electrodes (16a, 16b) can be the same size and shape (as in FIG. 2b), or indeed the second electrode (16b) could be smaller in surface area than the first electrode (16a). The essential element is that electrical activity is created in the region of the facial nerve at a point where it branches. As illustrated in FIGS. 2a and 2b, the apparatus of the present invention ensures that effective stimulation of the facial nerve will occur when the electrode pair (16a, 16b) is located just anterior to the tragus or the earlobe (i.e. by a distance of approximately 15 mm which is roughly equivalent to a finger width) in such a way that the mid-line of the electrode pair (16a, 16b) is substantially co-linear with a notional line (15) which runs anteriorly from the stylomastoid foramen through the earlobe. Whilst a posterior-anterior spacing of the electrode pair (16a, 16b) has been found to be most effective, the electrode pair (16a, 16b) could instead be spaced apart in the superior-inferior direction, or at any intermediate angle between the two.

In its broadest sense, the apparatus of the present invention comprises at least one transcutaneous stimulating electrode pair (16a, 16b) and a stimulation device (not shown) connectable thereto for providing a stimulating current whereby at least part of the apparatus is provided with a "location feature" adapted to interact, cooperate or align with one or more features of the ear (14). In all cases a feature of the ear is used as an anatomical reference to provide repeatable positioning of the electrodes (16a, 16b), anteriorly with respect to the ear (14), the electrodes being maintained in contact with a predetermined localised region of the face overlying branches of the facial nerve.

The apparatus further comprises an electrode carrier (20) functioning, in use, to support the electrodes (16a, 16b) in contact with the predetermined localised region of the face. If present in the apparatus, the electrode carrier (20), or a part thereof, may be provided with a "location feature" adapted to interact, cooperate or align with one or more features of the ear (14). One possibility is that the electrode carrier (20), or a part thereof, may be shaped or otherwise adapted to interact or align with one or more features of the ear (14), for example, with the earlobe and/or tragus. The electrode carrier (20) has a fixed and non-adjustable two-dimensional vector component in terms of the distance and direction between its "location feature" and the position of given points on the electrodes (16a, 16b).

Figure 3:
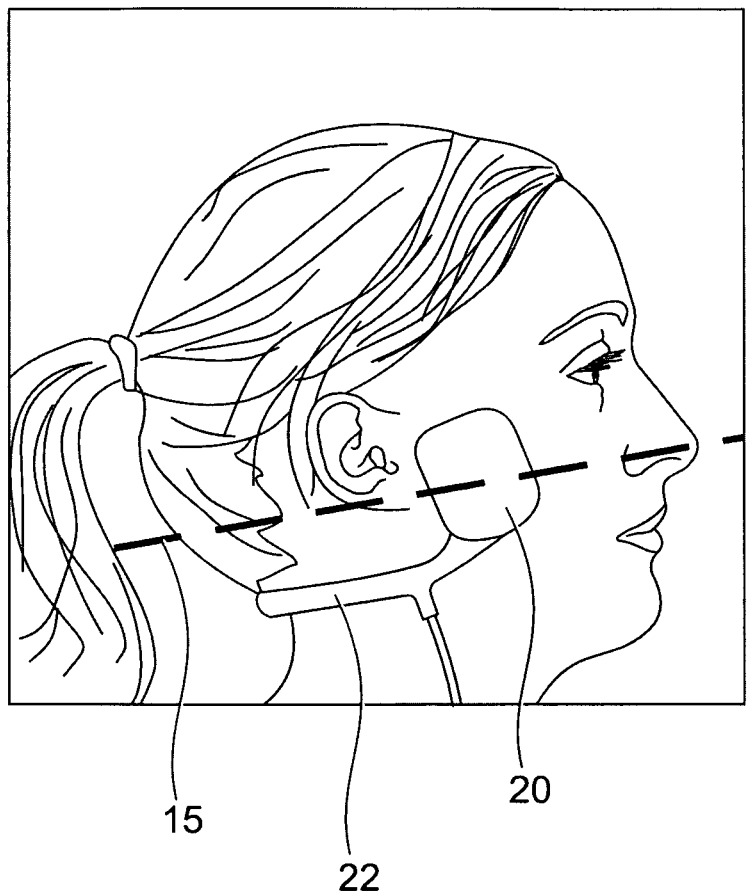
FIG. 3 shows apparatus according to an aspect of the present invention for providing repeatable and non-adjustable positioning of the electrodes of FIG. 2a or 2b with respect to the ear using the ear lobe and/or tragus as the anatomical reference.

A further possibility, an example of which is illustrated in the embodiment of FIG. 3, is that the apparatus also comprises a headband (22) which, in use, is arranged to extend around the back of a user's head and urge the electrode carriers (20) connected to its opposing distal ends, and its associated electrodes (16a, 16b), into contact with the desired localised regions of the face anterior to the ear (14). The headband (22), or a part thereof, is provided with a "location feature" adapted to interact or align with one or more features of the ear (14) in addition to, or instead of, any adaptation made to the electrode carrier (20) for this purpose. One possibility is that the headband (22), or a part thereof, may be shaped or otherwise adapted to interact or align with one or more features of the ear (14), for example, with the earlobe and/or tragus. The headband (22) has a fixed and non-adjustable two-dimensional vector component in terms of the distance and direction between its "location feature" and the position of any given points on the electrodes (16a, 16b).

Figure 4:
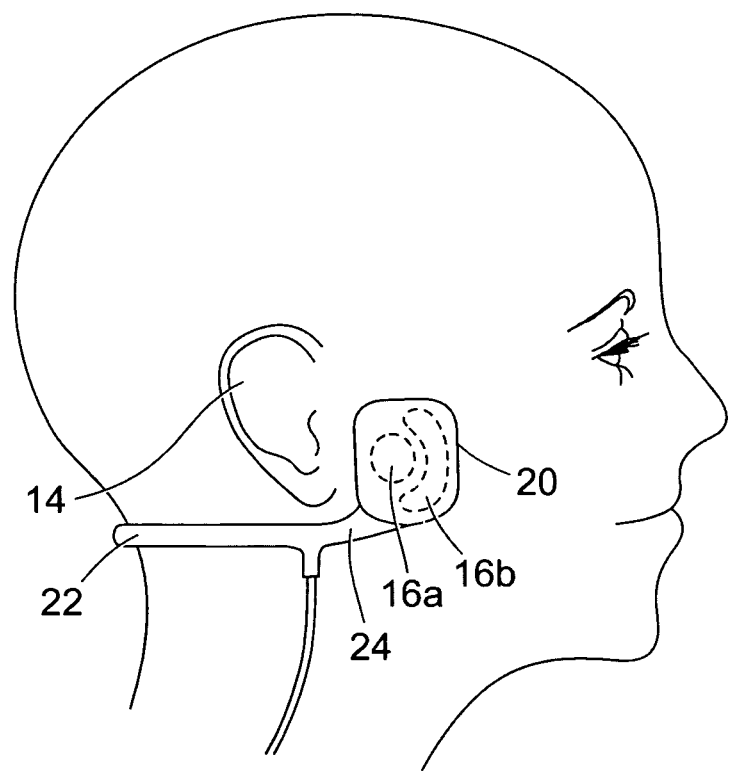
FIG. 4 shows a view of the apparatus of FIG. 3 whereby the arrangement of the electrodes is visible in dashed lines.
Figure 5:
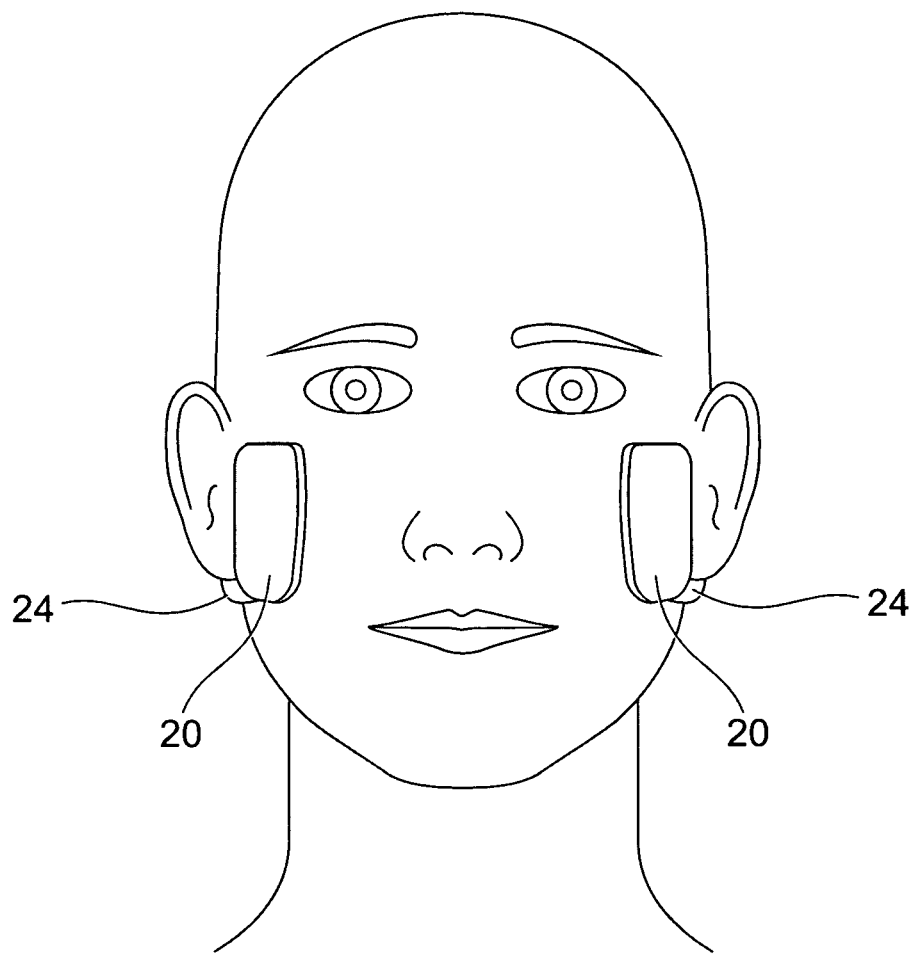
FIG. 5 shows a schematic front view of the apparatus of FIG. 3.

As shown in FIGS. 3-5, the apparatus of the present invention comprises a headband (22) provided with a non-adjustable bend or deviation (24) which connects it to the distal electrode carrier (20). The headband (22) takes the form of a resilient C-shaped band which, in use, locates around the back of the head in a generally horizontal orientation along a line below the earlobes where they join the head. The deviation (24) extends out of the general plane defined by the C-shaped plane of the headband (22). Advantageously, the non-adjustability of the headband limits the extent of anterior movement of the electrode pair towards the front of the face.

In use, the internal angle of the deviation (24) locates beneath, and optionally against, a lower peripheral region of the ear (14) proximate the earlobe which functions as an anatomical reference to provide repeatable and non-adjustable positioning of the electrodes (16a, 16b), with respect to the ear (14), to thus ensure electrical contact is made with the desired localised regions of the face just anterior to the earlobe and tragus of the ear (14). Ideally, the headband (22) and its deviation (24) lies approximately 10 mm below the earlobe thus positioning the electrode pair (16a, 16b) just anterior of the earlobe and the tragus.

Relative to the bottom of the earlobe, the ideal position of the centre of the first electrode (16a) is found by moving 30 mm±5 mm anteriorly and then up 15 mm±5 mm. The deviation (24) can be a sharp angle or a gradual curved part which ensures this relative displacement from the anatomical reference provided by the earlobe.

Figure 6:
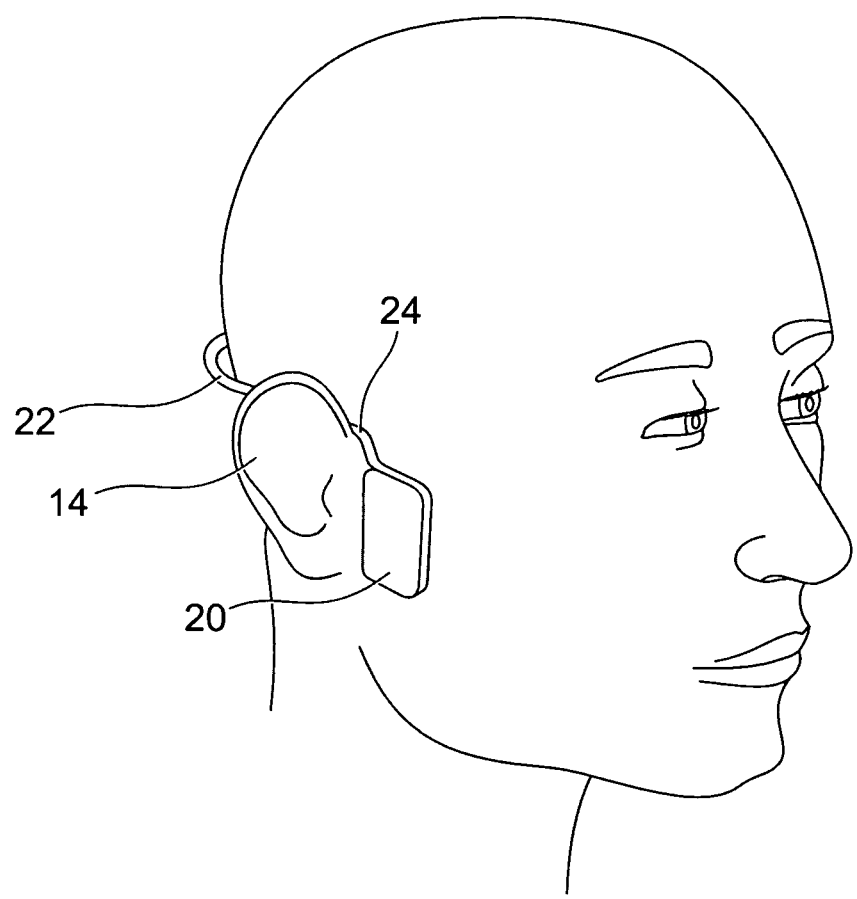
FIG. 6 is a view showing an alternative embodiment (not forming part of the present invention) whereby the upper part of the ear, where the auricle joins the head, is used as the anatomical reference.

FIG. 6 shows an alternative embodiment which is similar in many respects to that described above. However, the resilient C-shaped band locates around the back of the head in a generally horizontal orientation along a line coincident with the top of the ear (14), and the internal angle of the deviation (24) locates above, and optionally against, an upper peripheral region of the ear (14) proximate the point where the auricle meets the head. This part of the ear (14) also acts as an effective anatomical reference to provide repeatable and non-adjustable positioning of the electrodes, with respect to the ear (14), to ensure contact with the desired localised regions of the face anterior to the ear (14).

Figure 7:
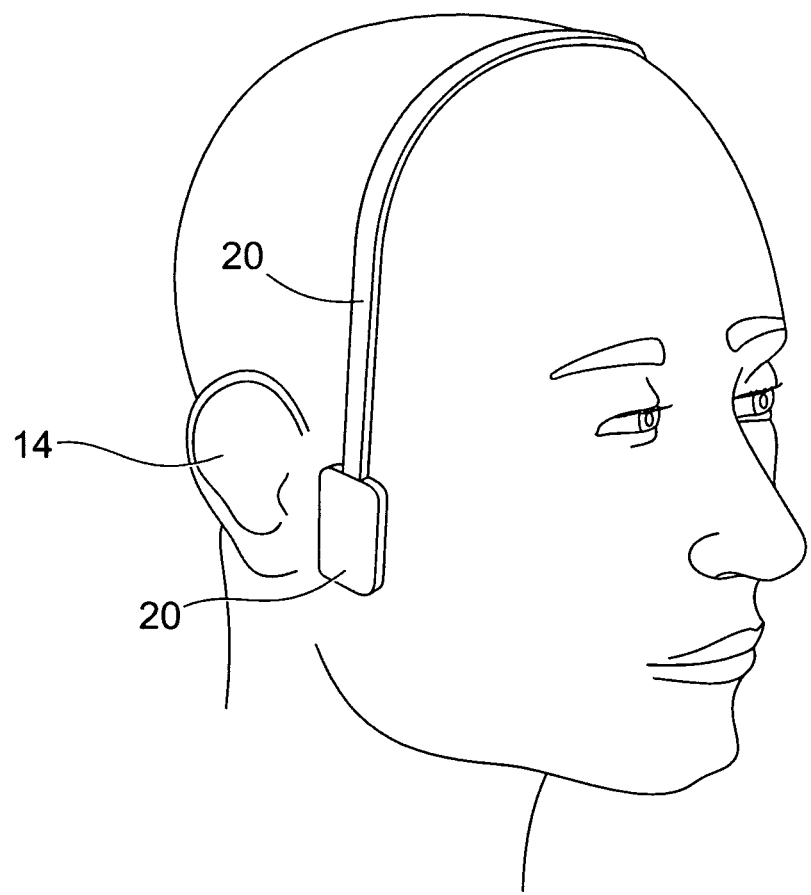
FIG. 7 is a view similar to that of FIG. 6, but showing a further alternative embodiment (not forming part of the present invention) whereby the tragus is used as the anatomical reference.

A further alternative embodiment (not forming part of the present invention) is shown in FIG. 7 whereby the resilient headband (22) locates around the top of the head in a generally vertical orientation along a line just anterior to the ear (14). The absence of a bend or deviation in this embodiment means that the headband (22) itself does not navigate around features of the ear (14). Instead, the electrode carrier (20) locates immediately beside or against an intermediate peripheral region of the ear (14) proximate the tragus. Whilst the tragus also acts as an equally effective anatomical reference to ensure correct lateral positioning of the electrodes, the advantage of the aforementioned embodiments is that the internal angle of the deviation (24) ensures correct lateral and longitudinal positioning of the electrodes. In the embodiment of FIG. 7, it is necessary to provide adjustability in the resilient headband (22) to allow for the greater degree of interpersonal variation in the over-the-head path length, and to ensure that the first electrode (16a) lies at the correct longitudinal position approximately 15 mm±5 mm from the bottom of the ear lobe.

Figure 8:
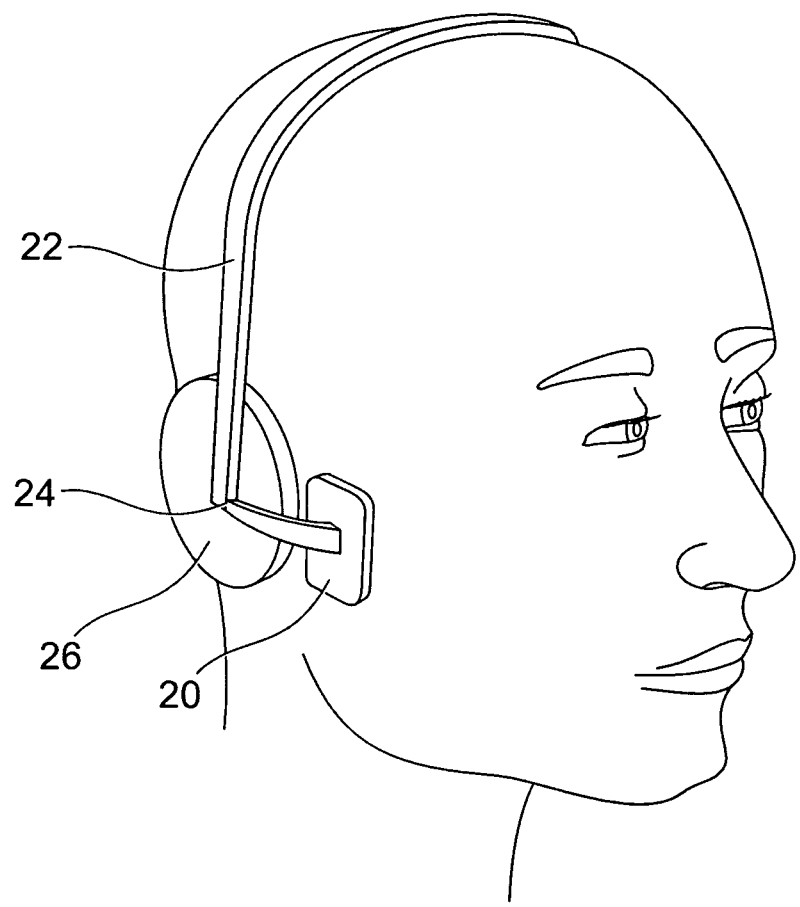
FIG. 8 is a view similar to that of FIGS. 6 and 7, but showing a yet further alternative embodiment (not forming part of the present invention) whereby the concha is used as the anatomical reference.

A yet further alternative embodiment (not forming part of the present invention) is shown in FIG. 8 whereby the resilient headband (22) locates around the top of the head in a generally vertical orientation along a line coincident with the ear canal. The resilient headband (22) may be provided with conventional earphones (26) which, in use, are urged against the concha. The resilient headband (22) is provided with a non-adjustable generally right-angled elbow bend (24) on each earphone near its point of attachment to the electrode carrier (20). Alternatively, a separate headband may depend from the earphone in a generally horizontal orientation along a line coincident with the middle of the ear, for example, over the tragus. In either case, the concha also acts as an effective anatomical reference to provide repeatable and non-adjustable positioning of the electrodes, with respect to the ear (14), to ensure electrical contact with the desired localised regions of the face anterior to the ear (14).

With regard to the embodiments of the present invention shown in FIGS. 3-5, in use, an end-user opens the C-shaped band (22) to a degree sufficient for it to pass forward from the back of the head below the ears. The C-shaped band is then gently released and the electrode carriers (20) locate over branches of the facial nerve on either side of the face. The C-shaped band (22) is designed to provide appropriate compression based on its inherent springiness. The compressive force, which ideally is approximately 5 to 7 N, is derived from the spring characteristics of the C-component of the band and the known displacement of the spring from its resting position when extended (opened) and positioned around the skull with its distal ends just anterior of the ears.

The shape and dimensions of the band (22) facilitates its positioning under the ears. When the band (22) is in place around that back of the neck below the ears, the deviation (24) on each arm presents the electrodes (16a, 16b) anterior to each ear. The width of the head is less below the ear than it is above the ear. Consequently, the C-shaped band can be smaller because it does not have to bypass a wider portion of the head in order to position its distal ends at a narrower position of the head.

To ensure accurate placement of the electrodes (16a, 16b) over the desired localised region of the face anterior to the earlobe and tragus, the end-user's sole task is to locate the internal angles of each deviation (24) of the C-shaped band (22) below, and optionally against, the underside of the ear lobes. Using the concept of triangulation, this simple task will inherently ensure that the electrodes (16a, 16b) are positioned correctly anterior to the ear.

With regard to the embodiment of FIG. 6, in use, an end-user opens the C-shaped band (22) to a degree sufficient for it to pass forward from the back of the head above the ears. This may require a greater opening force in view of the increased width of the head at this position. The C-shaped band is then gently released and the electrode carriers (20) locate over the facial nerve on either side of the face. To ensure accurate placement of the electrodes (16a, 16b) over the desired localised region of the face the end-user's sole task is to locate the internal angles of each deviation (24) above, and optionally against, the uppermost portion of the ear where the auricle meets the head.

With regard to the embodiment of FIG. 7 (not forming part of the present invention), in use, an end-user opens the C-shaped band (22) to a degree sufficient for it to pass down from the top of the head just anterior to the ears. The C-shaped band is then gently released and the electrode carriers (20) locate over the facial nerve on either side of the face. To ensure accurate placement of the electrodes (16a, 16b) over the desired localised region of the face the end-user's sole task is to locate the electrode carriers (20) beside, and optionally against, the tragus of the ear.

With regard to the embodiment of FIG. 8 (not forming part of the present invention), in use, an end-user opens the C-shaped band (22) to a degree sufficient for it to pass down from the top of the head anterior to the ears. The C-shaped band is then gently released and the electrode carriers (20) locate over the facial nerve on either side of the face. To ensure accurate placement of the electrodes (16a, 16b) over the desired localised region of the face the end-user's sole task is to locate the earphones (26) centrally on the concha.

The surface profile of the human head anterior to the ear is highly variable from person to person and therefore the electrode carriers (20) must be able to accommodate any undulations whilst maintaining a uniform pressure over the surface of the electrode. To allow the electrode carrier to adapt to the shape of an end-user's face the preferred solution, as shown schematically in FIGS. 9a-c, is to use an electrode carrier (20) which comprises a paddle of flexible rubber material (21) which is attached to the remainder of the apparatus by a flexible neck (23). Moreover, the paddle of flexible rubber material (21) is sufficiently flexible so as to readily accommodate deviations from a true planar surface.

The electrode carrier (20) comprises a conductive means (25) corresponding to each electrode (16a, 16b). In a preferred arrangement, the conductive means (25) is provided integrally within the electrode carrier (20) as regions of conductive flexible polymer. It is well established in the field of medical electrodes to add a conductive material such as carbon black to a polymer compound. The conductive sections (25) are moulded into the electrode carrier (20) at the time of manufacture. Alternatively, the conductive means comprises metallic contacts moulded into the paddle of flexible rubber material (21) with flexible wires (25) travelling through the flexible neck (23) into the adjoining electrode carrier (20). FIG. 4 shows one example of a lead extending from the C-shaped band (22) for connection to an external stimulation device (not shown).

It will be appreciated that the various embodiments of the present invention each provide several important distinctions and advantages over prior art facial stimulation apparatus. Firstly, known prior art devices fail to disclose apparatus with the following combination of features:

(i) the apparatus being provided with a "location feature" to interact, cooperate or align with one or more features of the ear; and (ii) the ear being used as an anatomical reference to provide repeatable positioning and, importantly, minimal positional adjustment of an electrode pair with respect to the said one or more features of the ear; and (iii) the stimulating electrodes of the electrode pair being maintained in contact with a predetermined localised region of the face just anterior to the ear; and (iv) the apparatus having a fixed, non-adjustable two-dimensional vector component in terms of the distance and direction between the "location feature" and any given points on the electrode pair.

The inventor of the present invention has realised that there is relatively little interpersonal variation in the positioning of the insertion of the branches of the facial nerve relative to several features of the ear. This is because the orifices which accommodate the facial nerve and the auditory canal, called the stylomastoid foramen and the auditory meatus respectively, are both located on the temporal bone, which is one of the constituent bones of the skull, just below and behind the ear. These orifices are relatively close together and the ear is attached to the head at the overlying auditory meatus. The ear therefore provides the ideal and unambiguous reference location for the stylomastoid foramen from which the facial nerve extends anteriorly and enters the face via the parotid gland. Features of the ear therefore provide an ideal landmark for locating an electrode over the facial nerve.

The facial nerve diverges after emerging from the stylomastoid foramen as indicated in FIG. 1. The electrodes in the apparatus of the present invention are therefore designed to interact with the facial nerve in a region where it diverges anterior to the ear. The optimal position for the first electrode is where its centre is located over the facial nerve anterior to the stylomastoid foramen and the earlobe. Even if the electrode is not ideally placed, provided some of it overlaps facial nerve branches anterior to the stylomastoid foramen and the earlobe then effective stimulation of the facial nerve branches can nevertheless be achieved.

As a consequence, it was further realised that by providing a tangible and readily identifiable "location feature" on a facial stimulation apparatus to assist its location relative to a particular feature of the ear (i.e. whereby the ear acts as an anatomical reference), the problem of inconsistent electrode placement by end-user's lacking sufficient anatomical knowledge could be overcome. In particular, it was found that by adapting the apparatus to provide a tangible "location feature" to assist with correct electrode placement for one end-user, this would also reliably position electrodes over the same predetermined localised regions of the face for all other end-users.

Hence, contrary to the accepted wisdom in the art, there is in fact a surprising advantage in providing no adjustability in the apparatus in terms of the relative distance between the anatomical reference point on the ear and the predetermined localised region of the face. Many prior art examples fail to recognise this fundamental point and have provided unnecessary and unreliable adjustability. In some cases, such as in the apparatus disclosed in the aforementioned WO 00/71075 (Maher & Johnson), the very adjustability of the apparatus actually precludes the location of the electrodes over the insertion of the facial nerve since the booms to which the electrodes are attached cannot be shortened to the extent that their distal ends lie sufficiently close to relevant area of the face just anterior to the ears.

Advantageously, the apparatus of the present invention requires no anatomical knowledge on the part of the end-user. The sole responsibility of the end-user is to position or align the relevant "location feature", adjacent to or in direct contact with an unambiguous anatomical reference point on the ear. In doing so, the electrodes will inevitably be correctly positioned on the face over the insertion of the facial nerves anterior to each ear.

A further advantage of the present invention is that a consistent inward pressure is applied to each electrode carrier (20) thus ensuring a reliable electrical contact with the skin. Advantageously, this is achieved without complicated arrangements of pivots or springs commonly found in prior art devices thus reducing manufacturing costs. The C-shaped band (22) of the present invention is arranged such that when its opposing distal ends are separated to an extent corresponding to the width of the head just anterior to the ear, its resilience ensures that adequate and equal inward pressure is applied to the respective electrode carriers (20) to maintain reliable electrical contact between each electrode (16a, 16b) and the skin.

A particular advantage of the under-ear arrangement of FIGS. 3-5 is that the head is at its narrowest at this point to allow unimpeded urging of the electrodes against the appropriate region on the face by the C-shaped band (22). This arrangement also has the advantage of limiting possible movement of the electrode pair (16a, 16b) in the anterior direction.

Modifications and improvements may be made to the foregoing embodiments without departing from the scope of the present invention as defined by the claims. For example, whilst the "location feature" described for each embodiment is defined by a mid-line or shaped portion of the electrode carrier (20) and/or the headband (22), other means of providing the "location feature" are possible. For example, the "location feature" may alternatively, or additionally, take the form of a tangible reference feature such as visually perceptible marker and/or a tactile reference such as change in surface texture of the relevant part of the apparatus intended to locate on, against or next to the anatomical reference point on the ear.

Whilst the headband (22) has been described and illustrated as having a bend or deviation (24) formed near its point of attachment to the electrode carrier (20), the bend or deviation (24) could be formed from two or more separate components connected together such that the distance and angle of the distal ends are fixed and non-adjustable once assembled.

Whilst four different anatomical features of the ear (14) have been described above as suitable anatomical references, any other feature of the ear (14) could be used provided that appropriately adapted apparatus is used to ensure correct placement of electrodes (16a, 16b). Also, the use of a combination of anatomical features of the ear (14) is not precluded.

The flexible paddle members (21) may connect to the electrode carriers (20) by means of a snap fit into a receptacle which carries conductive contacts which are crimped or soldered onto the wiring within each electrode carrier (20). The connection may take the form of a ball and socket joint which also provided an electrical connection between the two.

The apparatus of the present invention is connectable to an external stimulation device worn on another part of the body, for example by means of the electrical lead shown in FIG. 4. However, it is also possible to integrate the stimulator electronics and a power source such as a battery within the apparatus worn on the head. The apparatus could be rechargeable and furthermore could be operated wirelessly for a remote control means.

The final connection between the electrodes (16a, 16b) and the end-user's skin may be by means of an electrolyte. This can be as simple as a water based gel or more preferably one or more conductive and adhesive hydrogel patch shaped to match that of the electrode carrier (20). Separate patches matching the shape of each individual electrode (16a, 16b) can be provided. Alternatively, it is possible to use a single patch which covers both electrodes (16a, 16b) provided the lateral conductivity of the patch is low. This is achieved by using a thin patch such that the shunting impedance between the electrodes (16a, 16b) is high compared to the impedance of the circuit through the subject's skin.

What is claimed is:

1. Facial stimulation apparatus for applying an electrical current to human facial nerves, the apparatus comprising:
   (i) a C-shaped headband (22);
   (ii) two electrode carriers (20) nonadjustably attached to the headband (22);
   (iii) a pair of stimulating electrodes (16a, 16b) provided on each electrode carrier (20);
   (iv) a stimulation device connectable to the electrodes (16a, 16b) for providing a stimulating current thereto; and
   (v) a location feature associated with each electrode carrier for repeatable anatomical positioning of the apparatus with respect to an anatomical feature of each ear (14) of a human;
characterized in that:
   the headband (22) is non-adjustable in length and resilient;
   the electrode carriers (20) are connected to respective opposing distal ends of the headband (22), such that both electrodes of each electrode pair (16a, 16b) are configured to be urged against skin overlapping facial nerve branches (1, 2, 3, 4, 5) just anteriorly of each ear (14);
   wherein the location features are defined by respective non-adjustable bends or deviations (24) at said respective opposing distal ends of the headband (22), said bends or deviations (24) non-adjustably connecting the headband (22) to each electrode carrier (20) and extending out of the general plane within which the remainder of the headband (22) lies, thus ensuring inevitable positioning of each electrode pair (16a, 16b) over facial nerve branches just anteriorly of each ear (14), with respect to said anatomical feature.

2. Facial stimulation apparatus according to claim 1, wherein an additional location feature is defined by a mid-line of the electrode carrier (20) for anatomical referencing with an earlobe.

3. Facial stimulation apparatus according to claim 1, wherein an additional location feature is defined by a proximal edge of the electrode carrier (20) for anatomical referencing with a tragus.

4. Facial stimulation apparatus according to claim 1, wherein one electrode (16a) of each electrode pair has a different shape and/or surface area from the other electrode (16b) of the same electrode pair.

5. A cosmetic method of applying an electrical current to human facial nerve comprising the steps of:
   (i) providing apparatus comprising a non-adjustable and resilient C-shaped headband (22);
   (ii) providing two electrode carriers (20) nonadjustably attached to respective opposing distal ends of the headband (22);
   (iii) providing a pair of stimulating electrodes (16a, 16b) on each electrode carrier (20);
   (iv) providing a single stimulation device connectable to each electrode pair (16a, 16b) for providing a stimulating current thereto;
   (v) providing a location features associated with each electrode carrier, each location feature being defined by respective non-adjustable bends or deviations (24) at said respective opposing distal ends of the headband (22), said bends or deviations (24) non-adjustably connecting the headband (22) to each electrode carrier (20) and extending out of the general plane within which the remainder of the headband (22) lies;
   (vi) positioning the headband (22) on a human head by locating it around the back of the head such that it lies in a generally horizontal orientation whilst urging each electrode pair (16a, 16b) over facial nerve branches (1, 2, 3, 4, 5) just anteriorly of each ear (14); and
   (vii) repeatably positioning each bend or deviation such that it lies below, and is anatomically referenced to, an earlobe (24) thus causing each electrode pair (16a, 16b) on said electrode carriers (20) to inevitably be urged against skin overlapping facial nerve branches (1, 2, 3, 4, 5) just anteriorly of each ear (14) of a human, with respect to each earlobe.

6. A cosmetic method according to claim 5, wherein an additional location feature is defined by a mid-line of the electrode carrier (20) and the method comprises the step of positioning the mid-line such that it is aligned with, and is anatomically referenced to, the earlobe.

7. A cosmetic method according to claim 5, wherein an additional location feature is defined by a proximal edge of the electrode carrier (20) and the method comprises the step of positioning the proximal edge such that it lies adjacent, and is anatomically referenced to, a tragus.

* * * * *